US011977027B2

(12) United States Patent
Paulsen et al.

(10) Patent No.: US 11,977,027 B2
(45) Date of Patent: May 7, 2024

(54) DEVICE AND METHOD FOR DETERMINING THE DEPTH OF A SUBSURFACE FLUORESCENT OBJECT WITHIN AN OPTICALLY ABSORBING AND SCATTERING MEDIUM AND FOR DETERMINING CONCENTRATION OF FLUOROPHORE OF THE OBJECT

(71) Applicants: THE TRUSTEES OF DARTMOUTH COLLEGE, Hanover, NH (US); UNIVERSITY HEALTH NETWORK, Toronto (CA)

(72) Inventors: Keith D. Paulsen, Hanover, NH (US); David W. Roberts, Lyme, NH (US); Dennis Wirth, Hanover, NH (US); Brian C. Wilson, Toronto (CA); Mira Sibai, Toronto (CA)

(73) Assignees: THE TRUSTEES OF DARTMOUTH COLLEGE; UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 18/202,823

(22) Filed: May 26, 2023

(65) Prior Publication Data
US 2023/0324301 A1    Oct. 12, 2023

Related U.S. Application Data

(63) Continuation of application No. 17/516,490, filed on Nov. 1, 2021, now Pat. No. 11,662,315, which is a
(Continued)

(51) Int. Cl.
*G01B 11/22*    (2006.01)
*G01N 21/47*    (2006.01)
(Continued)

(52) U.S. Cl.
CPC ......... *G01N 21/6456* (2013.01); *G01B 11/22* (2013.01); *G01N 21/4795* (2013.01); *G01N 33/4833* (2013.01); *G01N 2201/062* (2013.01)

(58) Field of Classification Search
CPC .......... G01N 21/6456; G01N 21/4795; G01N 33/4833; G01N 2201/062; G01B 11/22
See application file for complete search history.

(56) References Cited

U.S. PATENT DOCUMENTS 6,321,111 B1 * 11/2001 Perelman ........... G01N 21/4795
                                                 250/358.1
7,960,707 B2    6/2011 Hall et al.
(Continued)

OTHER PUBLICATIONS

International Patent Application No. PCT/US2019/029421, International Search Report and Written Opinion dated Jul. 11, 2019, 14 pgs.
(Continued)

*Primary Examiner* — David P Porta
*Assistant Examiner* — Fani Polyzos Boosalis
(74) *Attorney, Agent, or Firm* — Cozen O'Connor

(57) ABSTRACT

A method and device for determining the depth and fluorophore concentration of a fluorophore concentration below the surface of an optically absorbing and scattering medium suitable for use in fluorescence-based surgical guidance such as in tumor resection is described. Long-wavelength stimulus light us used to obtain deep tissue penetration. Recovery of depth is performed by fitting measured modulation amplitudes for each spatial frequency to precomputed modulation amplitudes in a table of modulation amplitudes indexed by optical parameters and depth.

28 Claims, 8 Drawing Sheets

Related U.S. Application Data continuation of application No. 17/050,745, filed as application No. PCT/US2019/029421 on Apr. 26, 2019, now Pat. No. 11,162,900.

(60) Provisional application No. 62/663,158, filed on Apr. 26, 2018.

(51) Int. Cl.
  *G01N 21/64* (2006.01)
  *G01N 33/483* (2006.01)

(56) References Cited

U.S. PATENT DOCUMENTS

| | | | |
|---|---|---|---|
| 9,066,657 B2* | 6/2015 | Yazdanfar | A61B 5/0059 |
| 10,785,393 B2 | 9/2020 | Shen | |
| 11,162,900 B2* | 11/2021 | Paulsen | G01N 33/4833 |
| 2006/0184043 A1 | 8/2006 | Tromberg et al. | |
| 2016/0309068 A1 | 10/2016 | Nadeau et al. | |

OTHER PUBLICATIONS

Konecky, S.D., et al. "Spatial frequency domain tomography of protoporphyrin IX fluorescence in preclinical glioma models." Journal of Biomedical Optics 17(5), 056008 (May 2012).

* cited by examiner

DEVICE AND METHOD FOR DETERMINING THE DEPTH OF A SUBSURFACE FLUORESCENT OBJECT WITHIN AN OPTICALLY ABSORBING AND SCATTERING MEDIUM AND FOR DETERMINING CONCENTRATION OF FLUOROPHORE OF THE OBJECT

PRIORITY CLAIM

The present application is a continuation of U.S. patent application Ser. No. 17/516,490 filed Nov. 1, 2021, which is a continuation of U.S. patent application Ser. No. 17/050, 745, filed Oct. 26, 2020 now U.S. Pat. No. 11,162,900, which is a 35 U.S.C. § 371 filing of International Application No. PCT/US2019/029421 filed Apr. 26, 2019, which claims priority to U.S. Provisional Patent Application No. 62/663, 158 filed Apr. 26, 2018, all of which are incorporated herein by reference in their entirety.

GOVERNMENT RIGHTS

This invention was made with government support under grant no. R01 NS052274 awarded by the National Institutes of Health. The government has certain rights in the invention.

TECHNICAL FIELD

A method and device for determining depth and fluorophore concentration of fluorescent objects located below a surface of an optically absorbing and scattering medium is described. The method and device are suitable for use in fluorescence-based surgical guidance such as in tumor resection.

BACKGROUND

Surgery is used commonly as part of the treatment of patients with tumors. In many cases, the goal is to maximize the extent of tumor resection, while minimizing damage to surrounding heathy tissues to improve survival and quality of life. Preoperative radiological imaging such as magnetic resonance imaging (MRI) or X-ray computed tomography (CT) is often used to guide the procedure, for example to show the location of the tumor with reference to other anatomical structures. However, during surgery, tumors may shift in position, leading to loss of co-registration with pre-surgical images. In addition, it may be difficult to identify the true tumor margin. Near the end of surgery, it may also not be possible for the surgeon to visualize residual tumor that could regrow if not removed.

Hence, fluorescence imaging (fluorescence guided resection, FGR) during surgery is emerging as a valuable adjunctive technique to address these limitations.

FGR may be based on the natural fluorescence of the tissue, often called tissue autofluorescence. Alternatively, an exogenous fluorescent material ("fluorophore") may be administered to the patient to highlight the tumor. In this case the spectrum of fluorescent light emerging from the tissue upon illuminating the tissue with light of a suitable excitation wavelength is the combination of tissue autofluorescence plus fluorescence from the exogenous fluorophore at the concentration that it reaches in the particular tissue.

Different exogenous fluorophores have been investigated both in preclinical models and in clinical trials of different tumor locations and stages. For example, indocyanine green (ICG), that emits fluorescence in the near-infrared region of the spectrum is often used to image the perfusion of blood within tissue. For tumor imaging, and in particular for guiding surgery, a common fluorophore is protoporphyrin IX (PpIX) that is synthesized within cells upon administration of aminolevulinic acid (ALA). In general, this shows high contrast between tumor and normal host tissue. The PpIX absorbs at a range of wavelengths, from around 400 nm to around 630 nm, exciting a spectrum of fluorescence emission at around 700 nm. Absorption of PpIX is far stronger at the short-wavelength end of this absorption range than at the long end, as illustrated in FIG. 1B. Because of greater absorption efficiency and easier filtering of emissions from excitation light at wide separations, systems imaging ALA-induced PpIX fluorophore concentrations typically use short-wavelength, or "blue," light for excitation while observing deep red emissions light.

ALA-PpIX fluorescence image guidance is typically used, for example in brain tumor surgery, by incorporating a blue light source for excitation and red-to-near infrared fluorescence detection into a neurosurgical microscope. For other sites, the fluorescence imaging technology is incorporated into an endoscope or is "stand-alone", independent of other medical imaging devices. ALA-PpIX fluorescence image guidance has demonstrated clinical benefit by enabling more complete resection of the tumor near the end of surgery. For example, ALA-PpIX-based FGR of high-grade glioma using blue-light excitation has been shown to at least double the rate of complete resection and improve progression-free survival.

When fluorescence images are taken at a tissue surface, the strength of the fluorescence signal is affected by the attenuation of the excitation and emission light due to the optical absorption and scattering of the light by the tissue. This attenuation can be substantial and shows a complex wavelength dependence. As a result, a relatively weak measured fluorescence signal or low-brightness image taken at the tissue surface may be the result of either low concentration of the fluorophore or high absorption and/or scattering at the excitation and/or emission wavelengths. Conversely, a region of bright fluorescence intensity may be due to high fluorophore concentration and low absorption and scattering. The absolute concentration of the fluorophore, for a given administered dose for the fluorophore (or its precursor as in the case of ALA-PpIX) is an important marker of the presence of malignant cells or tissues so that resolving such ambiguities is of value.

Thus, measuring the absolute PpIX concentration in the tissue during resection can significantly improve the sensitivity and specificity of residual tumor detection, by better identifying fluorescent tissue that is not seen by qualitative visual assessment. This has been demonstrated using a fiberoptic probe that measures the fluorescence spectrum of light, at a single specific location the tissue surface. The spectrum of diffusely-reflected light is measured and analyzed to calculate the absorption coefficients ($\mu_a$) and the transport scattering coefficients ($\mu'_s$) of the tissue at the fluorescence excitation and detection wavelengths. After applying appropriate calibration factors, these data are then used as input to a model of light transport in tissue to convert the measured fluorescence signal into the true, or intrinsic, signal corrected for the confounding effects of unknown light attenuation by the tissue. The PpIX concentration in the tissue at the probe location is then recovered by spectrally un-mixing the known PpIX fluorescence spectrum from the tissue autofluorescence and from any photoproducts of PpIX that may have been generated during the surgery.

In this point-spectroscopic mode, quantitation of the PpIX concentration in the tissue has enabled enhanced resection rates in both low- and high-grade gliomas over and above the rates achieved using quantitative fluorescence image guidance alone. This technique is referred to here as quantitative point fluorescence spectroscopy, qFS.

SUMMARY

We will use ALA-PpIX fluorescence guided resection of brain tumor resection to demonstrate the present invention but it is understood that the method and device described herein are applicable to other fluorophores, including near-infrared fluorophores, and for different tumors and non-oncological applications.

Quantitative localized fluorescence spectroscopy has been extended to wide-field quantitative imaging, qFI, in which $\mu_a$ and $\mu'_s$ of the tissue are first mapped across the surgical field-of-view and then these data are applied to correct the measured fluorescence images on a pixel-by-pixel basis, analogously to the point-probe technique. One method to map the optical properties is by spatial frequency domain imaging (SFDI). This is a specific form of diffuse optical imaging that can produce images of $\mu_a$ and $\mu'_s$ parameters over large fields of view with submillimeter spatial resolution. In SFDI, sine-wave or other periodic patterns of light are projected onto the tissue surface, and the pattern of spatially-resolved diffuse reflectance from the tissue is imaged. This pattern has the same spatial frequency and phase as the projected pattern but intensity distribution is modulated by scattering and attenuation in the tissue.

Knowing these optical absorption and transport scattering maps across the surgical field of view, the effects of light attenuation on the detected fluorescence image are corrected for, analogously to qFS. After subtracting the tissue autofluorescence, an image of the absolute concentration of the PpIX at or near the tissue surface is generated. A device in which SFDI is incorporated into a hyperspectral fluorescence imaging system has been reported and the PpIX concentration in intracranial tumors in a glioma model in rats was calculated in the form of 2D maps, with an accuracy of about ±~10%, which is comparable to that of qFS. The minimum detectible concentration was about 13 ng/ml.

The methods and devices for qFS and qFI as defined above that apply rigorous analytical or numerical modeling of light propagation in tissue are distinct from f other methods and devices based on semi-empirical algorithms. For example, fluorescence images may be collected at two different excitation wavelengths or at two different detection wavelengths, and various ratio images can be generated from these. These methods and devices are intended to minimize or partly compensate for the effects of light attenuation and other factors that may affect the fluorescence image. However, they differ from the present invention because they do not enable the absolute fluorophore concentration in the tissue to be calculated and mapped.

When light at short wavelengths such as in the violet or blue region of the spectrum is used to excite the fluorophore, the limited penetration depth of this light in tissue restricts qFI to superficial tumors, up to a depth of about 1 mm. The purpose of the present invention is to extend the quantitative capability of qFI to deeper tissues lying beyond the resection bed surface to image both the depth of sub-surface tumor and the fluorophore concentration therein. The present invention differs from the above qFI methods and devices in that the fluorophore concentration is calculated for fluorophore lying substantially below the tissue surface.

BRIEF DESCRIPTION OF THE DRAWINGS

The elements in the figures are not to scale.

DETAILED DESCRIPTION OF THE EMBODIMENTS AND SUPPORTING DATA

Figure 1A:
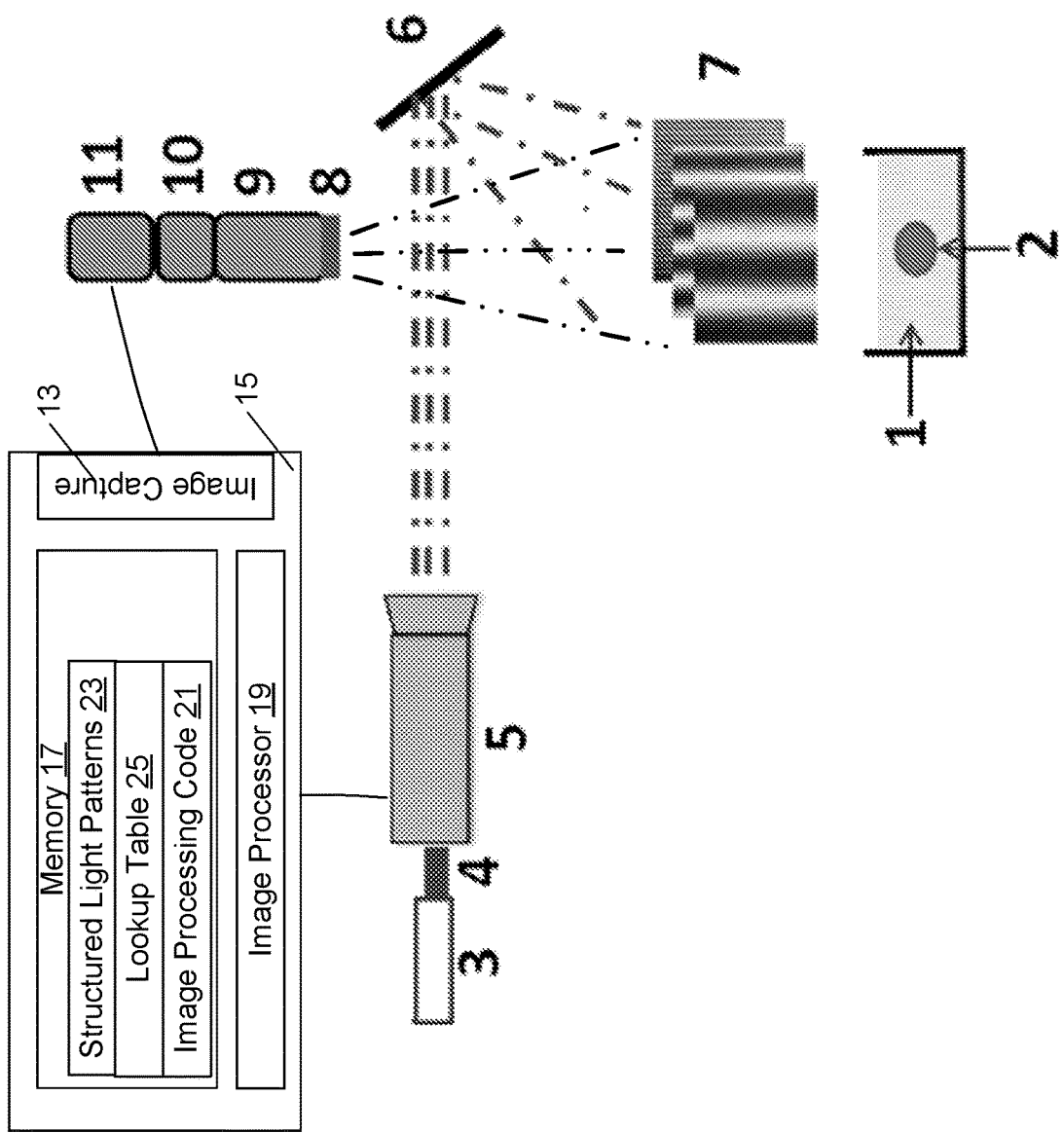
FIG. 1A is a schematic of a benchtop hyperspectral SFDI instrument used on tissue-simulating phantoms and gliomas or other cancers as described herein.

There are at least two complementary approaches to determine the depth of subsurface fluorescent tumor, in a form of imaging referred to here as dFI. In one method and device, fluorescence images are taken at multiple different excitation wavelengths. The images are then ranked according to the expected effective penetration depth of each wavelength of light in the tissue, a form of intensity thresholding is applied, and a topographic image is generated that displays the depth of the top layer of the subsurface fluorescent tumor. For PpIX this method and device determined the depth of a subsurface fluorescent object with an accuracy of about ±0.5 mm up to a depth of about 3 mm in brain tissue.

The second method and device, which has also been demonstrated for PpIX, is to excite the fluorescence with red light that penetrates much deeper into the tissue, and then to form images at several different wavelengths of the fluorescence emission. Since longer wavelengths are less attenuated by the overlying tissue, the detected fluorescence spectrum at each point in the image is distorted to a degree that depends on the depth from which the fluorescent light originates. For PpIX this method and device have given a depth accuracy of about ±1 mm up to a depth of about 8 mm in brain tissue. Red light is light generally of 630 nanometers or longer wavelength.

The present invention differs from these two methods and devices for dFI in that the subsurface fluorophore depth images are here calculated from a series of SFDI images taken in fluorescence mode under long wavelength excitation (e.g. red light in the case of PpIX) The depth estimate is then based on the rate of decay of the fluorescence-mode SFDI signal modulation with increasing spatial frequency.

Qualitative ALA-PpIX FGR using red light to excite PpIX has been reported in 30 patients with various intracranial tumor pathologies, adapting a fluorescence-enabled neurosurgical microscope to this excitation wavelength. This has demonstrated enhanced tumor resection by enabling detection of sub-surface PpIX fluorescence up to an estimated depth of about 5 mm, compared to about 1 mm under blue-light excitation. However, the PpIX absorption is 1-2 orders of magnitude lower near 635 nm than at 405 nm and, due to the much longer optical paths at around 635 nm, the detected fluorescence intensity depends strongly on the fluorophore concentration, depth and distribution and is also affected by the tissue absorption and scattering. The negative impact of these uncontrolled factors on quantifying the fluorophore concentration in subsurface tumor motivates the development and validation of methods and devices to separate the depth of the fluorophore from its concentration at that depth, as in the present invention.

Hyperspectral fluorescence imaging can also be used to estimate sub-surface PpIX depth, using the fact that the logarithmic ratio of two fluorescence images at different emission wavelengths is approximately linear with fluorophore depth and with optical penetration depth. Tumor depths from about 1 to 9 mm could be recovered within ±1 mm. However, additional constraints were needed to estimate the fluorophore concentration at depth. Fluorescence-mode SFDI improves spatial localization of the fluorophore by gating the penetration depth of the excitation light according to spatial frequency, thereby facilitating depth-resolved imaging. This is to be contrasted with planar illumination, i.e. illumination of the tissue with uniform unpattern light, where the collected signal comprises fluorescence originating from all depths but weighted towards the surface.

SFDI-enabled depth-resolved fluorescence imaging has been reported. Multiple spatial-frequencies of red-light SFDI were used to excite PpIX in sub-surface intracranial tumors in mice. A 3D tomographic approach was applied to recover the PpIX distribution and concentration. This differs from the present invention, since the tumor depth had to be known a priori for this reported method, whereas in the present invention this depth is calculated from the measured data in an individual patient without prior knowledge of the sub-surface depth of the fluorophore.

The present method and device determine the sub-surface fluorophore depth by exploiting SFDI's depth encoding capabilities from just below the surface up to about 9 mm with red-light excitation of PpIX at around 635 nm. In the present invention the images of both the depth and the fluorophore concentration at that depth for tumor lying below the accessible tissue surface (e.g. the resection bed) are determined. The goal here is not to produce a full 3D tomographic distribution of the fluorophore in the tissue, but rather to provide topographic images indicating the depth of fluorescent tumor closest to the resection cavity surface, as well as the fluorophore concentration at that depth. Both separately and in combination, this information should help the surgeon make a more informed decision on whether or not to continue resection in a particular region of the surgical field. This method is referred to here as qdFI.

To encode the fluorophore depth, patterned red light is projected onto the sample and the spatially-modulated fluorescence images are collected by a spectrally-resolved camera. The rate of decrease of the fluorescence modulation is calculated. The optical absorption and transport scattering coefficient values of the tissue are determined by a separate SFDI procedure using broad-band light and imaging the diffuse reflectance patterns from the tissue. These data are used, together with this rate of decrease, to calculate the subsurface depth of the fluorescent object. The images of tissue absorption and transport scattering are then also used in a forward model of light propagation in an optically turbid medium to calculate the concentration of the fluorophore at this depth in each pixel of the image.

This disclosure therefore relates to fluorescence guided surgery, and in particular concerns quantitative fluorescence assessment. Rather than relying on the qualitative visual view provided to the surgeon the technology estimates quantitative levels of fluorophore concentration, in this case, at depth below the immediate surgical surface. The disclosure includes methods to quantify the concentration of fluorophore in tissue for guiding surgery. Quantitative fluorescence imaging as taught herein is more sensitive and more accurate than relying on the surgeon's visual perception of fluorescence. Data shows that fluorescence which is to visible to the surgeon can represent resectable tumor in neurosurgery.

At least two complementary approaches have been presented to determine the depth of subsurface fluorescent tumor, in a form of imaging referred to here as dFI. In one method and device, fluorescence images are taken at multiple different excitation wavelengths. The images are then ranked according to the expected effective penetration depth of each wavelength of light in the tissue, a form of intensity thresholding is applied, and a topographic image is generated that displays the depth of the top layer of the subsurface fluorescent tumor. For PpIX this method and device determined the depth of a subsurface fluorescent object with an accuracy of about ±0.5 mm up to a depth of about 3 mm in brain tissue.

The second method and device, which has also been demonstrated for PpIX, is to excite the fluorescence with red light that penetrates much deeper into the tissue, and then to form images at several different wavelengths of the fluorescence emission. Since the longer wavelengths are less attenuated by the overlying tissue, the detected fluorescence spectrum at each point in the image is distorted to a degree that depends on the depth from which the fluorescent light originates. For PpIX this method and device have given a depth accuracy of about ±1 mm up to a depth of about 8 mm in brain tissue.

The present invention differs from these two methods and devices for dFI in that the subsurface fluorophore depth images are here calculated from a series of SFDI images taken in fluorescence mode under long wavelength excitation (e.g. red light in the case of PpIX) The depth estimate is then based on the rate of decay of the fluorescence-mode SFDI signal modulation with increasing spatial frequency.

Qualitative ALA-PpIX FGR using red light to excite PpIX has been reported in 30 patients with various intracranial tumor pathologies, adapting a fluorescence-enabled neurosurgical microscope to this excitation wavelength. This work (published by the Inventors) has demonstrated enhanced tumor resection by enabling detection of sub-surface PpIX fluorescence up to an estimated depth of about 5 mm, compared to about 1 mm under blue-light excitation. However, the PpIX absorption is 1-2 orders of magnitude lower than at 405 nm and, due to the much longer optical paths at around 635 nm, the detected fluorescence intensity depends strongly on the fluorophore concentration, depth and distribution and is also affected by the tissue absorption and scattering. The negative impact of these uncontrolled factors on quantifying the fluorophore concentration in subsurface tumor motivates the development and validation of methods and devices to separate the depth of the fluorophore from its concentration at that depth, as in the present invention.

Hyperspectral fluorescence imaging can also be used to estimate sub-surface PpIX depth, using the fact that the logarithmic ratio of two fluorescence images at different emission wavelengths is approximately linear with fluorophore depth and with optical penetration depth. Tumor depths from about 1 to 9 mm could be recovered within ±1 mm. However, additional constraints were needed to estimate the fluorophore concentration at depth. Fluorescence-mode SFDI improves spatial localization of the fluorophore by gating the penetration depth of the excitation light according to spatial frequency, thereby facilitating depth-resolved imaging. This is to be contrasted with planar illumination, i.e. illumination of the tissue with uniform unpattern light, where the collected signal comprises fluorescence originating from all depths but weighted towards the surface.

SFDI-enabled depth-resolved fluorescence imaging has been reported. Multiple spatial-frequencies of red-light SFDI were used to excite PpIX in sub-surface intracranial tumors in mice. A 3D tomographic approach was applied to recover the PpIX distribution and concentration. This differs from the present invention, since the tumor depth had to be known a priori for this reported method, whereas in the present invention this depth is calculated from the measured data in an individual patient without any prior knowledge of the sub-surface depth of the fluorophore.

Longwave qdFI

The present method and device determine the sub-surface fluorophore depth by exploiting SFDI's depth encoding capabilities from just below the surface up to about 9 mm with red-light excitation of PpIX at around 635 nm. In the present invention the images of both the depth and the fluorophore concentration at that depth for tumor lying below the accessible tissue surface (e.g. the resection bed) are determined. The goal here is not to produce a full 3D tomographic distribution of the fluorophore in the tissue, but rather to provide topographic images indicating the depth of the fluorescent tumor closest to the resection cavity surface, as well as the fluorophore concentration at that depth. Both separately and in combination, this information should help the surgeon make a more informed decision on whether or not to continue resection in a particular region of the surgical field. This method is referred to here as qdFI.

To encode the fluorophore depth, patterned red light is projected onto the sample and the spatially-modulated fluorescence images are collected by a spectrally-resolved camera. The rate of decrease of the fluorescence modulation is calculated. The optical absorption and transport scattering coefficient values of the tissue are determined by a separate SFDI procedure using broad-band light and imaging the diffuse reflectance patterns from the tissue. These data are used, together with this rate of decrease, to calculate the subsurface depth of the fluorescent object. The images of tissue absorption and transport scattering are then also used in a forward model of light propagation in an optically turbid medium to calculate the concentration of the fluorophore at this depth in each pixel of the image.

We disclose the following methods and devices for qdFI. These methods and devices are illustrated by the example of PpIX but are not limited to this fluorophore. With suitable adjustment and knowing the fluorescence excitation and emission spectra, they may be applied to other fluorophores working across the ultraviolet-visible-near infrared ranges of the optical spectrum.

Specific apparatus and experiments is described together with results illustrating the performance of method and device. However, the method and device may be applied to other experimental conditions, including fluorescence-guided surgery in patients. Neither are the method and device restricted to brain tumors such as gliomas. Neither are the methods and devices restricted to the application of guiding tumor surgery, since they may be applied to determining the depth and concentration of any subsurface fluorophore within an optically absorbing and scattering medium.

An object containing a fluorescent material (the fluorophore) of known fluorescence excitation and emission spectra is located below the surface of a homogeneous medium of unknown optically absorbing and scattering properties. The surface of the medium is illuminated with known patterns of spatially-modulated light, each pattern having a different known spatial frequency, f Two different forms of illumination are used one after the other in either sequence In the first form, referred to here as fluorescence-mode SFDI, the illumination light is at a wavelength or range of wavelengths known to excite the fluorophore and to provide sufficient penetration into the medium to interact with the fluorescent object, for example red light to excite PpIX fluorescence in tissue, such as 632 nm wavelength red light that excites a fluorescence peak at 705 nm, also red light, this peak lying between 700 and 710 nanometers. The images of fluorescence at the tissue surface is collected. In the second form, referred to here as reflectance-mode SFDI, the illumination light is spectrally broad band and images of the diffusely-reflected light from the tissue is collected at wavelengths of interest. In alternative embodiments, other fluorophores may be used with red or infrared excitation light and red or infrared fluorescent emissions light.

Figure 1B:
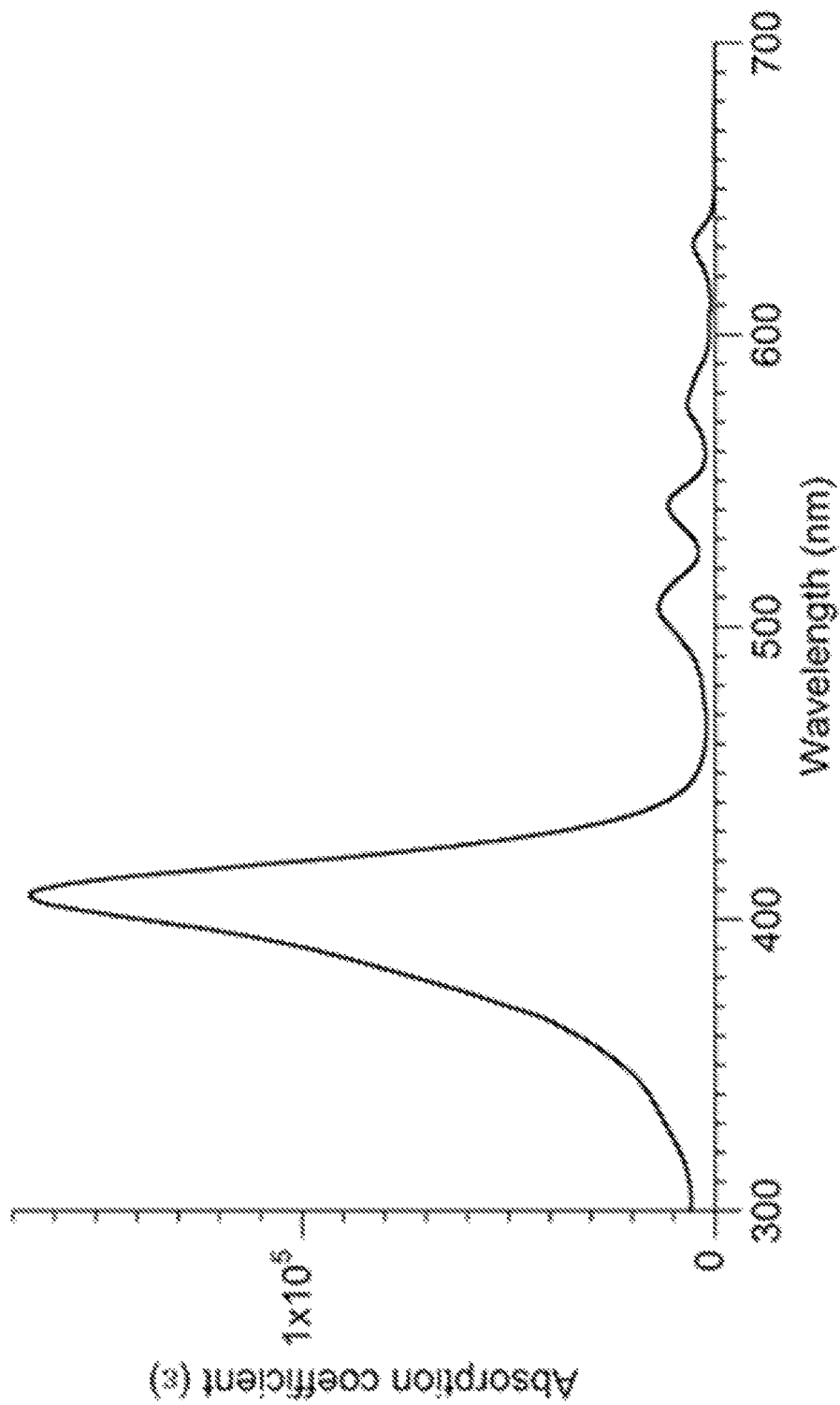
FIG. 1B is a graph illustrating absorption of protoporphyrin IX (PpIX) versus wavelength, showing that absorption of excitation wavelength light at short wavelengths is dramatically higher than at long wavelengths near the 632-nanometer wavelength used for excitation in the present system.

A system constructed for demonstrating qdFI, integrating hyperspectral imaging and SFDI in a single device, is illustrated in FIG. 1. The system operates to localize a sub-surface PpIX fluorescent inclusion 2 in a tissue-simulating phantom 1, or a glioma or other cancer in tissue. Light from a 632 nm LED light 3 is shown as an example of one of the several LED sources that may be activated. This light is a coupled by a light guide 4 to a digital light projector 5 onto a mirror 6 that reflects the spatially-modulated light pattern 7 onto the surface of the phantom 1. The spatially-modulated fluorescence images are filtered by a 650 nm long-pass filter 8 and passed through relay lenses 9 and then through a liquid crystal tunable filter 10 to a CCD camera 11. The system includes 6 LED light sources centered at 390, 440, 475, 512, 586 and 632 nm each with 20 nm bandwidth (Spectra X, Lumencor, Beaverton, OR, USA), of which one example is shown in the figure. Different central wavelengths and bandwidths could be selected to match other fluorophores. After passing through a liquid light guide 4 (LGG0338, ThorLabs, Montreal, Canada), the light is reflected by a spatial light modulator, DLP, 5 (Digital Micromirror Device, 0.55XGA Series 450, Texas Instruments, Dallas, TX, USA) onto the surface of the medium 1. All LEDs are turned on simultaneously to simulate white-light reflectance-mode SFDI to map the optical absorption and transport scattering coefficients of the tissue. In fluorescence-mode SFDI only the 632 nm LED is activated. The intensity of each LED is selected to optimally cover the dynamic range of the detector while avoiding saturation. The imaging sub-system consists of a 14-bit CCD detector array 11 (Pixelfly, PCO AG, Kelheim, Germany) connected to a visible-range liquid crystal tunable filter 10 (LCTF: Varispec-07-02, Perkin Elmer. Inc, Waltham, MA, USA) by a 1:1 relay C-mount lens 9, giving a field of view of 5 cm by 5 cm with 2.0 cm depth of field at the focal plane. A 650 nm long-pass filter 8 (FELH0650, Thorlabs, Montreal, Canada) is used to block the scattered red excitation light from the medium during fluorescence-mode imaging. Two-by-two binning of the images enhances the signal-to-noise of the fluorescence images with reasonable acquisition times (50-1000 ms.) per spatial frequency.

The CCD detector array 11 serves as a digital camera and provides images to an image capture or image receiving unit 13 in image processing unit 15. Within the image processing unit 15 is a memory 17 and an image processor 19. Image processor 19 is configured by image processing machine readable instructions of code 21 and structured light spatial patterns 23 in memory 17. Image processing code 21 is configured to use a lookup table 25 of precomputed predicted fluorescence modulation for concentrations of fluorophore located at a plurality of depths below the surface of the medium for each spatial frequency of the plurality of spatial frequencies.

Figure 2:
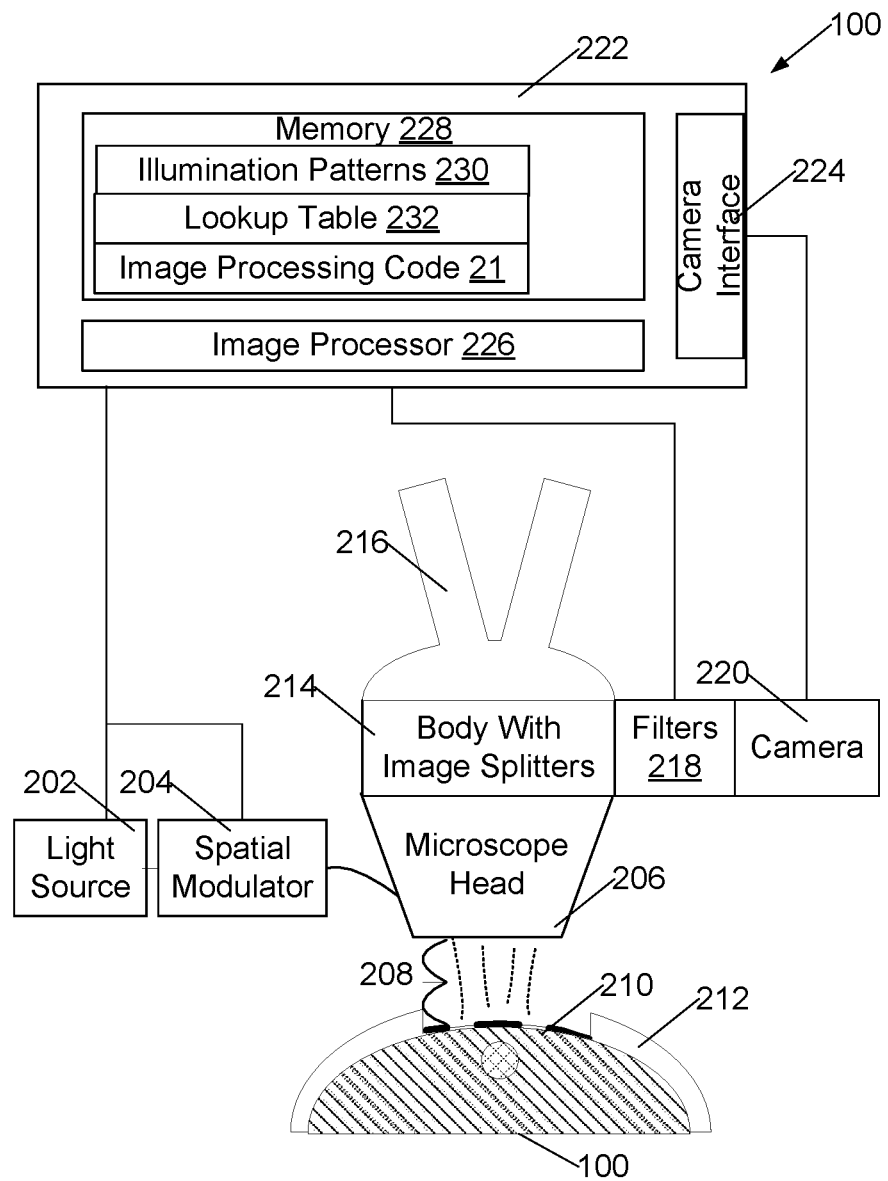
FIG. 2 is a block diagram of an alternative instrument for using qdFI during surgery, such as brain surgery for removal of gliomas.

An alternative embodiment of a system 200 configured to use qdFI is illustrated in FIG. 2, this system 200 is integrated with a surgical microscope for use in surgery. Light sources 202 feed through a spatial modulator 204, in an embodiment a projector based on a digital micromirror device. Patterned light is coupled to a microscope head 206 where it is focused and projected as light 208 onto a surface of tissue being inspected, such as brain tissue 210 beneath an opened skull 212 during surgery. Light from tissue 210 is received by microscope head 206 where it is focused and magnified, then enters microscope body 214 where a beamsplitter allows portion of received light to be viewed through eyepieces 216 by a surgeon, and a portion diverted through filters 218 into an electronic camera 220 where images are captured. Captured images from electronic camera 220 are fed to a digital image processing system 222 through a camera interface 224. The images are processed as described below with reference to FIG. 3 in an image processor 226 operating under control of machine readable instructions in memory 228. Memory 228 also contains illumination light patterns, which the image processor 226 may provide to spatial modulator 204 to generate spatially modulated light having predetermined spatial frequencies; in an embodiment the illumination light patterns include patterns with 0.1, 0.3, 0.5, 0.6, 0.8 and 1.0 lines per millimeter.

Figure 3:
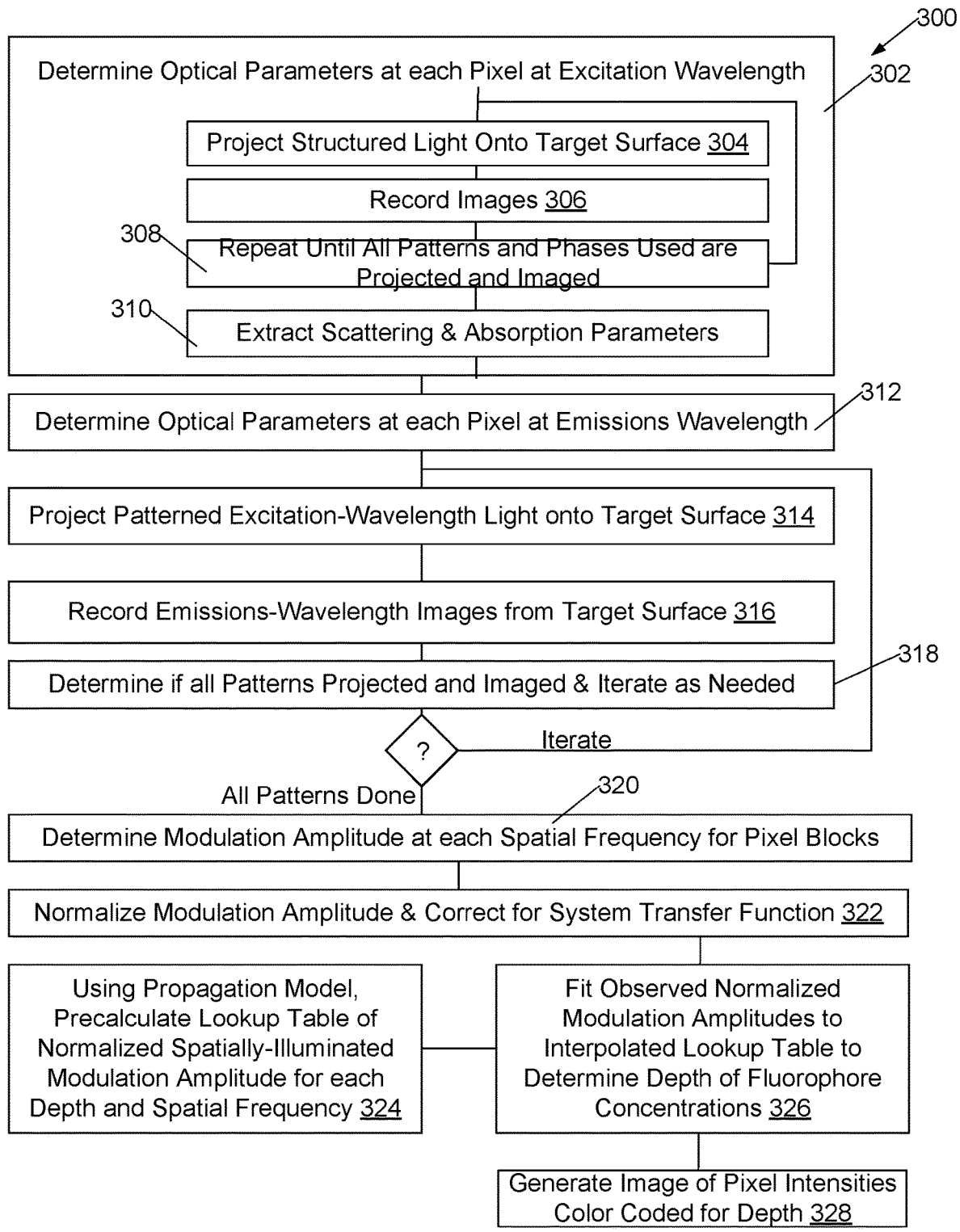
FIG. 3 is a flowchart of a method of operating the instruments of FIGS. 1 and 2 to perform qdFI and present images of use in analyzing pathological specimens or of indicating tumor tissue to a surgeon so that the surgeon may remove the tumor tissue during surgery.

Both systems of FIG. 1A and FIG. 2 operate using the method 300 of FIG. 3. To determine 302 optical parameters, including absorption coefficients and scattering coefficients at excitation wavelength, a surface of the medium or tissue is illuminated by projecting 304 a broad beam of light at an excitation wavelength of the fluorophore onto the surface using a spatially modulated pattern comprising alternating high and low intensity regions at a spatial frequency of one of the predefined patterns. Light received from the surface is imaged 306 in camera and recorded in the image processor, these images contain a pattern of diffusely reflected light emitted by the surface of the medium to form an excitation wavelength image. The steps of projecting light and imaging are repeated 308 at at least two additional spatial frequencies, such that all 6 available illumination light patterns having a defined spatial frequency are used including three having spatial frequency between 0.2 and 0.8 mm−1. Light at each spatial frequency is projected at more than one spatial phase, effectively shifting the light and dark bars of the spatially modulated light patterns so that all portions of the surface of the medium are illuminated in at least one phase of each pattern. A model of light propagation in an optically absorbing and scattering medium is used to calculate 310 an absorption coefficient and transport scattering coefficient of the medium at the excitation wavelength of the fluorophore at pixels of the excitation wavelength images.

Optical parameters at pixels are then determined at an emissions wavelength of the fluorophore expected to be present in inclusions within the medium, such as PpIX within tumors in brain tumors after ALA administration. In an embodiment, this is done by repeating steps of illumination at the emissions wavelength with spatially modulated light at a plurality of phases, recording images, and extracting parameters from the images as done at the excitation wavelength; in an alternative but less precise embodiment this is done by extrapolation from the stimulus wavelength parameters.

Then, while illuminating 314 with spatially modulated patterns at excitation wavelength, fluorescent emissions images of the surface of the medium are recorded 316 at a plurality of spatial frequencies, in embodiments the same plurality of spatial frequencies used while obtaining optical parameters are used by iterating 318 patterns sequentially. From these images, measured modulation amplitudes are extracted 320 at the plurality of spatial frequencies for pixel blocks, such as 15×20 pixel blocks, in the fluorescent emissions images recorded at the plurality of spatial frequencies; these modulation amplitudes are then normalized 322.

Prior to obtaining images, a lookup table 232 containing predicted fluorescence modulations for concentrations of fluorophore located at a variety of depths below the surface of the medium has been computed 324 for each spatial frequency of the plurality of spatial frequencies using a light propagation model.

The measured modulated amplitudes obtained at the plurality of spatial frequencies for pixel regions at the plurality of spatial frequencies are then fit 326 to the precomputed values in the lookup table to determine depth of the concentration of fluorophore. Once the depth of the concentration of fluorophore is determined, the depth and at least the absorption parameter are used to compensate for absorption, an image representing concentration and depth may be generated, such as an image with brightness representing quantity of fluorophore and color representing depth.

In embodiments, the excitation wavelength is less than 100 nanometers shorter than the emissions wavelength, such as 632 nanometer stimulus wavelengths with 705 nanometer emissions wavelengths.

First Example of Operation

A system according to FIG. 1A projects six spatial patterns sequentially at spatial frequencies of 0, 0.05, 0.1, 0.2, 0.27 and 0.38 mm$^{-1}$. These particular frequencies are selected to illustrate the method. Other combinations could be used if they provide a sufficient range of modulation of the detected spatial light pattern. Spatially- and spectrally-resolved images are collected at each spatial frequency in both reflectance mode and in fluorescence mode and analyzed.

Each periodic pattern of light is a spatially modulated pattern, for purposes of this document a spatially modulated pattern is a pattern having multiple, alternating, light and dark bars across a field of view, the light and dark bars having a spatial frequency equal to an inverse of a pitch of the dark bars. Sine-wave spatially modulated patterns include patterns where, if a line is drawn perpendicular to the bars of the pattern and light intensity is plotted along the line, light intensity varies sinusoidally along the line from a minimum at center of dark bars to a maximum at center of light bars. In an alternative embodiment, six patterns of structured light are projected in sequence at spatial frequencies of 0.1, 0.3, 0.5, 0.6, 0.8, and 1 mm−1. In embodiments, at least three spatial frequencies between 0.2 and 0.8 mm−1 are used at three spatial phases for extraction of absorption and transport scattering coefficients of the medium at both an excitation wavelength of the fluorophore PpIX and at an emissions wavelength of the fluorophore PpIX. In addition, in some embodiments a solid high intensity pattern is projected.

In one demonstration of the method and device, liquid phantoms were prepared to simulate the optical absorption and transport scattering coefficients of the tissue of interest across the appropriate wavelength range. These phantoms included Intralipid, a lipid-protein suspension of known optical scattering, as well a green absorbing dye of known extinction coefficient (absorption coefficient per unit concentration) and concentration. The Intralipid and dye concentrations were selected to be have absorption and transport scattering coefficients at around 635 and 705 nm that are typical of normal brain tissue, these wavelengths representing, respectively, the longwave PpIX fluorescence excitation wavelength and PpIX emission wavelengths. A region of fluorescence 2 containing a concentration of PpIX fluorophore, was positioned at a variable distance below the surface of the phantom to simulate, for example, a subsurface tumor. In an embodiment this included a transparent cylindrical inclusion (3.2 mm inner diameter, 4.8 mm outer diameter) passing through the phantom and parallel to the surface, and filled with phosphate buffered serum containing PpIX, and either Intralipid or blood at concentrations that yielded optical properties like those of the bulk medium, but with the added fluorophore PpIX. Green dye was used instead of rat blood to simulate tissue absorption in the bulk medium, because of the limited supply of blood available. The sub-surface depth of the fluorescent inclusion was altered by removing or adding liquid to the container, keeping a fixed distance between the instrument and the inclusion. Phantom preparation and measurements were repeated three times for all experiments. Table 1 lists the optical coefficients used in the phantom.

TABLE 1

Liquid phantom optical properties at the excitation (632 nm, 'x') and detection (705 nm, 'm') wavelengths, and PpIX concentration in the inclusion

| $\mu_{a,x}$ (mm$^{-1}$) | $\mu'_{s,x}$ (mm$^{-1}$) | $\mu_{a,m}$ (mm$^{-1}$) | $\mu'_{s,m}$ (mm$^{-1}$) | PpIX concentration (µg/ml) |
|---|---|---|---|---|
| 0.019 | 1.17 | 0.001 | 1.0 | 10 |
| 0.029 | 1.74 | 0.0015 | 1.5 | 10 |
| 0.038 | 2.32 | 0.002 | 2.0 | 15 |

In a second demonstration of the method and device, minced ex vivo bovine muscle was used to represent more realistic biological conditions. The tissue was placed in a container like that used for the liquid phantoms and a thin cylindrical inclusion (1.6 mm inner diameter, 3.2 mm outer diameter) containing a fixed PpIX concentration of 5 µg/ml was placed on top. Additional tissue then covered the inclusion to 3 different depths (2.5, 4.5, 9 mm), and triplicate images were collected at each depth. A smaller inclusion diameter was used than in the liquid phantoms to minimize air gaps between the inclusion and the tissue that could disturb the light pattern in the tissue.

Reflectance-mode SFDI imaging was used to map the absorption and transport scattering properties of the phantoms. Each of the 6 spatial frequencies, f, from 0 to 0.38 mm$^{-1}$ were projected onto the phantom surface for each of 3 spatial phases, $$\phi_i = \left[0, \frac{2\pi}{3}, \frac{4\pi}{3}\right].$$

Since the excitation wavelength used here was 632 nm and the LCTF had limited sensitivity above 680 nm, the optical properties around the PpIX emission wavelength band were not directly recovered. Rather, the hemoglobin absorption and Intralipid reduced scattering coefficients were extrapolated to 705 nm. White-light SFDI was performed both at the beginning and end of each experiment to confirm that there were no changes in the phantom optical properties due, for example, to settling of the Intralipid or blood.

In fluorescence mode only the 632 nm source was used, projecting sinusoidal patterns at the same spatial frequencies as above. Alternative embodiments with light sources between 620 and 640 nanometers are expected to produce similar results to the experiment's 632 nanometer light source. A planar fluorescence image of the inclusion in air was also captured at the beginning as well as at the end of each experiment to measure any signal loss due to photobleaching or possible separation of Intralipid and blood in the inclusion itself. The container was then filled with 200 ml of bulk medium and withdrawn stepwise (5 ml=1 mm change in depth) until the fluorescence from the inclusion was just detectable above background (signal/background >1.5). This was taken to represent the maximum detectable depth. The fluorophore depth is defined here as the distance between the phantom surface and the top of the inclusion. Planar and SFD fluorescence images were then acquired for each depth, integrating over 660-720 nm. The liquid medium was removed or added randomly to vary the depth without introducing systematic bias.

The measured data from the phantom were analyzed as follows to calculate the subsurface depth, z, of the inclusion in the medium. Firstly, a 10 by 20 pixel (~2.4 mm by 4.8 mm) region of interest at the center of the inclusion was selected to determine the modulation amplitude, Mf, as a function of fat 705 nm. Mf depends on both the fluorophore and the imaging system. Hence, at each unknown depth, Mf was normalized to the DC modulation amplitude (f=0), so that this was independent of the fluorophore concentration or quantum yield. The measured modulation amplitude was then corrected by the modulation transfer function of the imaging system, $MTF_{system}$ (x,y,z,f). Thus, for a fluorescent object at depth z and irradiated with unit light intensity at the fluorescence excitation wavelength, the normalized modulation amplitude is given by $$Mf(x,y,f)_z = MTF_{system}(x,y,f)_z \times F_m(x,y,f)_z, \quad (1)$$

where $F_m(x,y,f)_z$ is the normalized spatially-resolved diffuse fluorescence in the frequency domain.

Using diffusion theory, normalized and corrected spatially-illuminated modulation amplitude $F_m$ was calculated as a function of f for a range of depths z (0 to 30 mm in 0.05 mm increments) and for a range of optical absorption and transport scattering coefficients. A look-up table of modulation amplitudes indexed by absorption and transport scattering coefficients and frequency was created from this set of data.

The normalized modulation amplitude in the phantom was determined as a function of spatial frequency from the fluorescence-mode SFDI measurements. The optical absorption and transport scattering coefficients of the phantom at the fluorescence emission wavelength were determined from the reflectance-mode SFDI measurements. Using linear interpolation between the values in the look-up table, a least-squares fit was performed between i) the measured modulation amplitude versus spatial frequency and ii) the corresponding predicted curve based on the measured optical coefficients. In this fit, the fluorescent inclusion depth was the free variable to be determined.

Knowing thereby the value of z, the PpIX concentration at this depth in each image pixel was calculated from the measured unmodulated fluorescence image (f=0), corrected for the effects of absorption and scattering of the fluorescence excitation and emission light by the intervening tissue. This correction was obtained by forward modeling of light propagation in the medium, using diffusion theory with the measured optical absorption and transport scattering coefficients as input.

The results of these experiments in the tissue-simulating liquid phantoms and the ex vivo tissue phantom were as follows.

Figure 4:
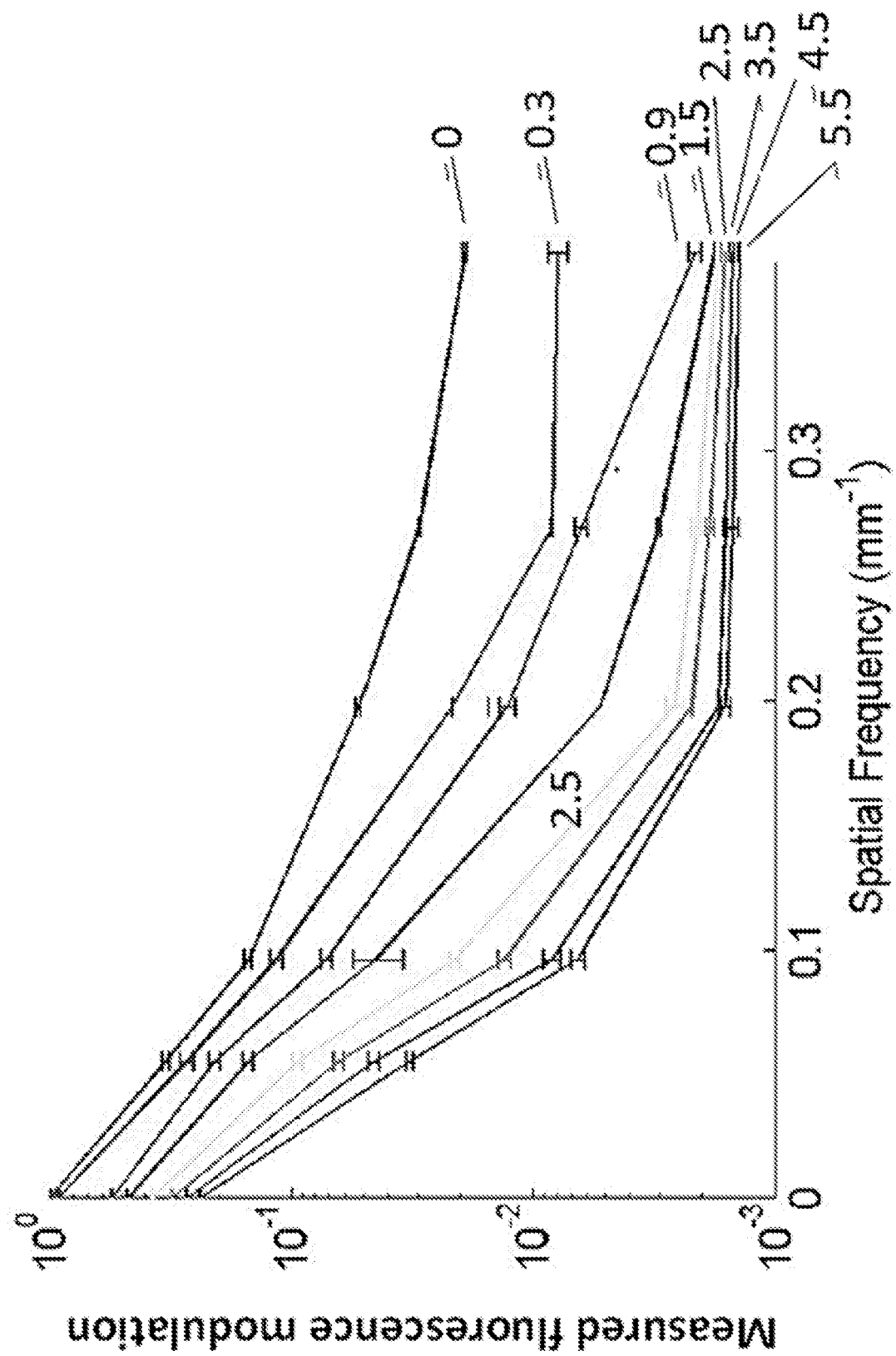
FIG. 4 is a graph of the measured normalized modulation amplitude of the fluorescence signal at 705 nm as a function of the spatial frequency of the incident 632 nm excitation light for different depths of the fluorescent object below the surface of the liquid phantom. The depths in mm are indicated on each curve. The fluorescent object contained 10 μg/ml of PpIX mixed with blood and Intralipid to simulate tissue optical properties of $\mu_a$=0.001 lines per millimeter (mm$^{-1}$) and $\mu'_s$=1 mm$^{-1}$ at 705 nm. Error bars are the standard deviation across three replicates.

The modulation of the fluorescent intensity pattern measured at the surface of one of the liquid phantoms when illuminated with 632 nm light at different modulation frequencies, as shown in FIG. 4, demonstrate a critical aspect of the invention, namely the fact that the rate of decrease of the fluorescence modulation with increasing spatial frequency is dependent on the depth of the fluorescent inclusion below the surface of the optically absorbing and scattering medium.

Figure 5A:
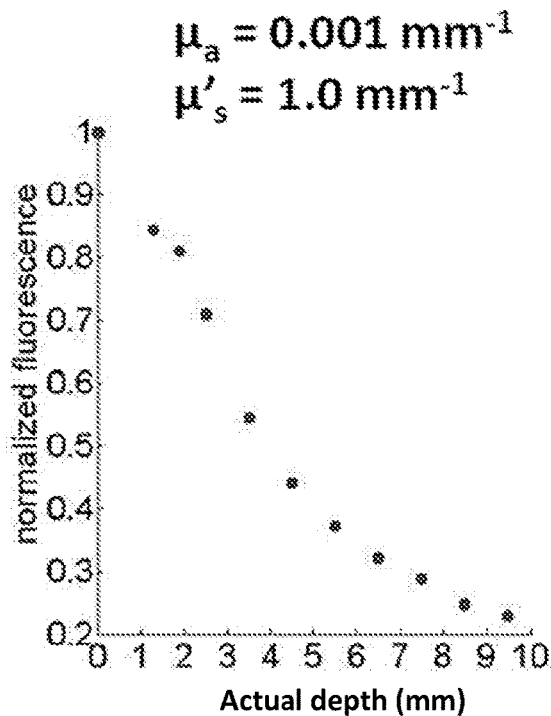
FIG. 5A-5C shows representative plots of the fluorescence modulation versus inclusion depth for different combinations of optical absorption and transport scattering coefficients of the phantom at 705 nm and for a particular spatial frequency f.
Figure 5B:
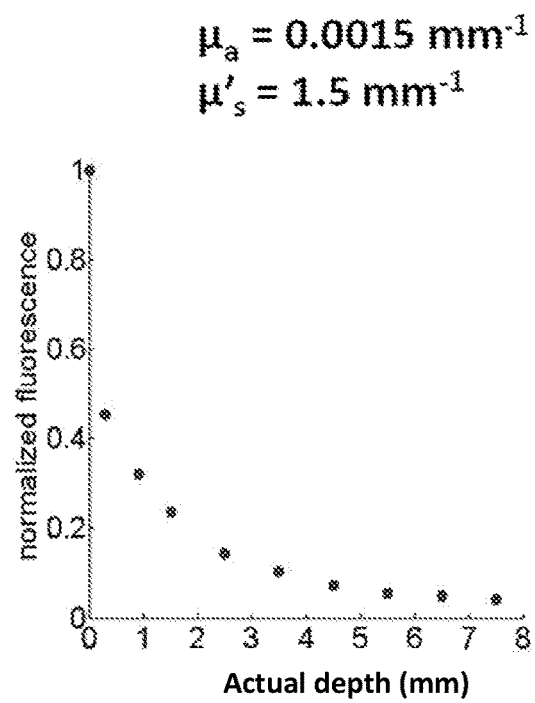
Figure 5C:
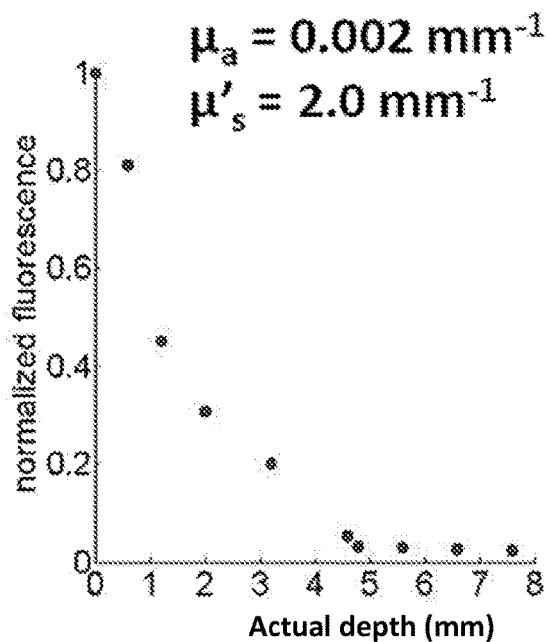

Examples of plots of fluorescence modulation versus fluorophore depth are shown in FIG. 5A-5C and demonstrate that the plots depend on the particular combination of absorption and transport scattering coefficients of the medium at the fluorescence emission wavelength. This then shows that it is necessary, for example using reflectance-mode SFDI imaging, to also measure these optical coefficients so that the depth of the inclusion can be calculated from the measured fluorescence modulation versus spatial frequency.

Figure 6A:
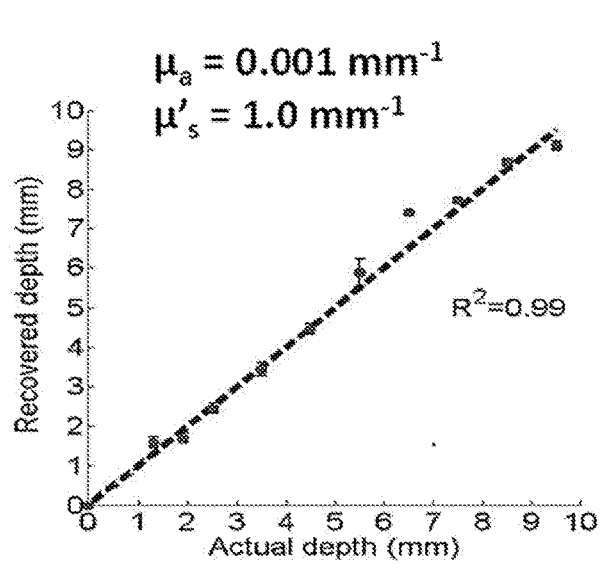
FIG. 6A-6C shows plots of the calculated depth versus the actual depth of the fluorescent inclusion for phantoms of different absorption and transport scattering coefficients. Error bars are the standard deviation from 3 replicates. The line of best fit is also shown together with the $R^2$ goodness of fit.
Figure 6B:
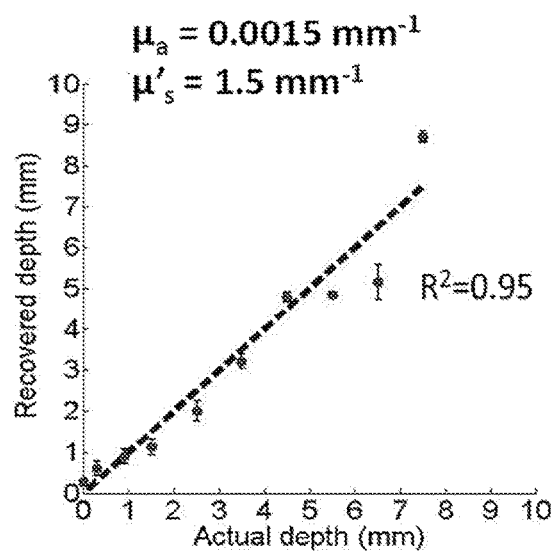
Figure 6C:
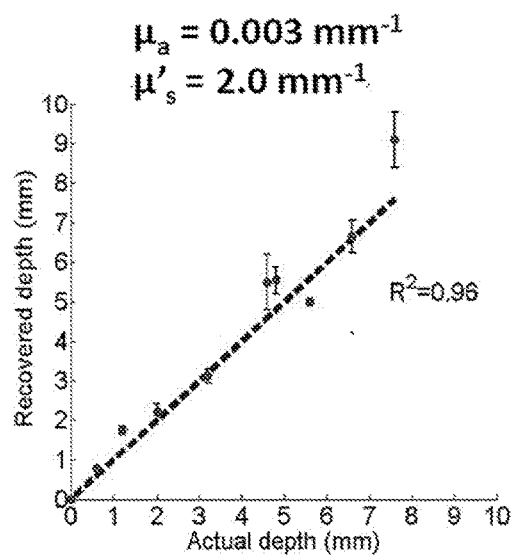

FIG. 6A-6C shows examples of the scatter plot of calculated depth versus the actual depth of the fluorescent inclusion below the surface of the phantom. The goodness of fit, $R^2$, to the line of equality was >0.95 in all cases. These results demonstrate that the depth can be determined, within an average uncertainty of ±0.42 mm. The maximum depth that could be measured within this level of uncertainty ranged from 5.5 to 7.5 mm depending on the phantom optical properties and on the PpIX concentration. The uncertainty in the depth measurement increased to ±1.5 mm at larger depths due to lower signal-to-background ratio.

Figure 7A:
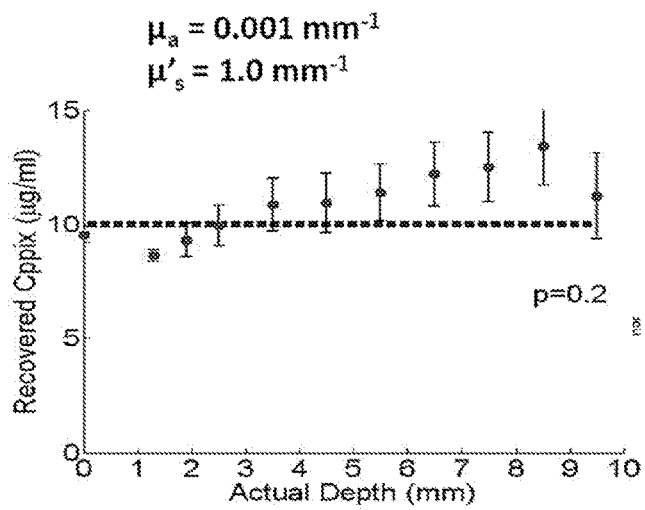
FIG. 7A-7C shows plots of the calculated PpIX concentration versus the actual depth of the fluorescent inclusion for phantoms of different absorption and transport scattering coefficients. The true value of the PpIX concentration is indicated by the horizontal line in each plot. Error bars are the standard deviation from 3 replicates. The p values indicate whether or not the calculated concentrations are statistically different from the actual concentrations.
Figure 7B:
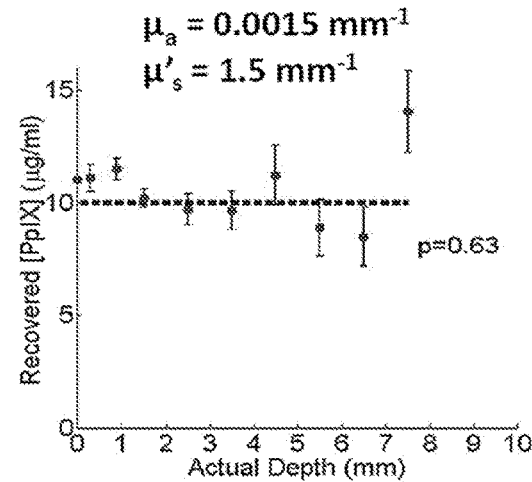
Figure 7C:
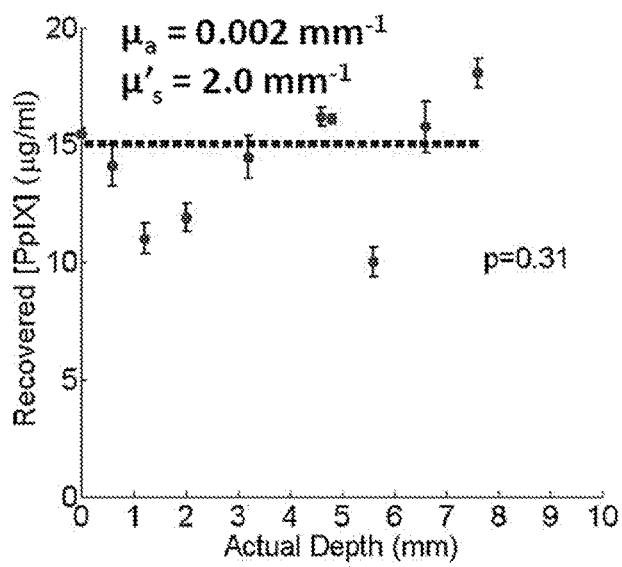

FIG. 7A-7C shows examples of the corresponding graphs of PpIX concentration in the subsurface inclusion and comparison with the actual concentration used in the experiments. The p values indicate that the calculated PpIX concentrations at different depths are not statistically different from the actual values in the subsurface fluorescent inclusion.

TABLE 2

Depth of PpIX concentration estimations for one phantom ($\mu_{a,m}$ = 0.002 mm$^{-1}$, $\mu'_{s,m}$ = 2 mm$^{-1}$) at an inclusion depth of 1.75 mm for varing PpIX concentration

| PpIX concentration (µg/ml) | 5 ± 0.007 | 7.5 ± 0.011 | 11 ± 0.015 | 15 ± 0.02 |
|---|---|---|---|---|
| Recovered depth (mm) | 2.28 ± 0.21 | 1.74 ± 0.20 | 2.0 ± 0.10 | 1.6 ± 0.11 |
| Recovered PpIX concentration (µg/ml) | 5.5 ± 0.6 | 8.2 ± 1.0 | 11.8 ± 0.5 | 15.6 ± 1.0 |

The results for the ex vivo tissue model are summarized in Table 3. The measured tissue optical properties, for excitation at 632 nm and detection at 705 nm, averaged over three locations near the inclusion, were $\mu_{ax}$=0.012±0.0007, $\mu'_{s,x}$=2.74±0.14, $\mu_{a,m}$=0.0046±0.00014 and $\mu'_{s,m}$=2.24±0.085 mm$^{-1}$. The recovered depths were within 10% of the nominal depths except at 9 mm, where the demodulated images had limited contrast (signal-to-background=1.8). The derived PpIX concentrations were within 15% of actual values for the first two depths, increasing to 40% at the largest depth.

TABLE 3

Summary of the estimated depth and PpIX concentration in ex vivo tissue with PpIX concentration of the inclusion = 5 µg/ml.

| Nominal depth (mm) | 2.5 | 4.5 | 9 |
|---|---|---|---|
| recovered depth (mm) | 2.3 ± 0.02 | 5.0 ± 0.07 | 6.48 ± 0.03* |
| recovered PpIX concentration (µg/ml) | 4.88 ± 0.32 | 6.4 ± 0.85 | 7.04 ± 0.78* |

*indicates p < 0.05

The results from the tissue-simulating phantoms with relatively high PpIX concentration (FIG. 5) show that the fluorophore depth and concentration are somewhat overestimated at large depths (7-9 mm). Conversely, the studies in ex vivo tissues (Table 3) indicate that the depth and PpIX concentration are underestimated at large depths (9 mm) when the inclusion had a relatively low fluorophore concentration of 5 µg/ml. This different behavior according to PpIX concentration was also seen in the subsurface depth technique of Kolste et al. Nevertheless, in all cases the errors in recovering both depth and the PpIX concentration were markedly reduced at higher signal-to-background (>1.5), the background being due, for example, to tissue autofluorescence. For a minimum signal-to-background ratio of 2, the depth was recovered to within ±0.45 mm and the PpIX concentration within ±10% of the actual values at 95% confidence level for PpIX-rich tumors located from just below the surface up to a maximum depth of 5-9 mm, depending on the tissue turbidity. At low signal-to-background ratio the depth was recovered within ±1 mm, while the PpIX concentration was recovered within an average accuracy of ±25%.

Further improvements of modifications to the method and device may be envisaged. Firstly, the calibration procedure described above adds to the steps required. Alternatively, multiple fluorescent inclusions can be encapsulated in gels and spaced laterally at different depths for imaging simultaneously to provide the instrument calibration.

Secondly, other improvements would reduce the acquisition time and increase the sensitivity to detect lower fluorophore concentrations at larger depths. For example, the red LED excitation source may be replaced by a higher power diode laser at a similar wavelength. The visible-range LCTF may be replaced by an LCTF with high near-infrared transmission (for example, Varispec SNIR/NIRR, Perkin Elmer. Inc, Waltham, MA) or other spectral filters that are efficient in the near-infrared range. A more sensitive imaging detector system such as an EM-CCD camera would improve the sensitivity and reduce the acquisition time. Direct computation of $\mu_{a,m}$ and $\mu'_{s,m}$ at all wavelengths with reflectance-mode SFDI would then be possible instead of extrapolating these values from 632 nm, as was done in the experiments reported above. Fast quantitative mapping of optical properties is possible with single snapshot SFDI, as recently reported. This approach could be incorporated into the present invention.

Combinations

It is anticipated that the various concepts herein disclosed can be combined in various ways. Among combinations anticipated by the inventors are:

A method designated A for determining a depth of a concentration of fluorophore lying beneath a surface of an optically absorbing and scattering medium including illuminating a surface of the medium with a broad beam of light at an excitation wavelength of the fluorophore using a first spatially modulated pattern comprising alternating high and low intensity regions at a first spatial frequency between 0.1 and 1 $mm^{-1}$, the first spatially modulated pattern projected onto the surface of the medium at a plurality of different phases. While so illuminated, the method continues with imaging diffusely reflected light emitted by the surface of the medium to form an excitation wavelength image for each phase of the plurality of different phases of the first spatially modulated pattern. The method continues with illuminating the surface of the medium with a broad beam of light at the excitation wavelength of the fluorophore using a second spatially modulated pattern comprising alternating high and low intensity regions at a second spatial frequency between 0.1 and 1 mm−1, the second spatially modulated pattern projected onto the surface of the medium at a plurality of different phases, the second spatially modulated pattern having a different spatial frequency than the first spatially modulated pattern, and imaging a pattern of diffusely reflected light emitted by the surface of the medium to form an excitation wavelength image for each phase the plurality of different phases of the second spatially modulated pattern. The images are processed by applying a model of light propagation in an optically absorbing and scattering medium to calculate an absorption coefficient and transport scattering coefficient of the medium at the excitation wavelength of the fluorophore at pixels of the excitation wavelength images. The method also includes determining emissions wavelength optical parameters coefficients at pixels. The method illuminates the surface of the medium with spatially modulated patterns at the excitation wavelength, recording fluorescent emissions wavelength images of the surface of the medium at a third spatial frequency; and while illuminating the surface of the medium with spatially modulated patterns at the excitation wavelength, recording fluorescent emissions wavelength images of the surface of the medium at a fourth spatial frequency. Once the emissions wavelength images are recorded, the method continues with extracting measured modulated amplitude at each of the third and fourth spatial frequencies for pixel regions in the fluorescent emissions wavelength images recorded at the third and fourth spatial frequencies. The method includes predicting modulated amplitude in images for concentrations of fluorophore located at a plurality of depths below the surface of the medium for each of the third and fourth of spatial frequencies, and fitting the measured modulated amplitude at the third and fourth spatial frequencies for the pixel regions to corresponding predicted modulated amplitudes to determine depth of the concentration of fluorophore. The third and fourth spatial frequencies comprise at least two spatial frequencies between 0.1 and 0.1 mm−1.

A method designated AA including the method designated A where the excitation and emissions wavelengths are red or infrared wavelengths greater than or equal to 630 nanometers.

A method designated AB for determining a depth of a concentration of fluorophore lying beneath a surface of an optically absorbing and scattering medium including illuminating a surface of the medium with a broad beam of light at an excitation wavelength of the fluorophore using a first spatially modulated pattern comprising alternating high and low intensity regions at a first spatial frequency between 0.1 and 1 mm−1, the first spatially modulated pattern projected onto the surface of the medium at a plurality of different phases. While so illuminated, the method continues with imaging diffusely reflected light emitted by the surface of the medium to form an excitation wavelength image for each phase of the plurality of different phases of the first spatially modulated pattern. The method continues with illuminating the surface of the medium with a broad beam of light at the excitation wavelength of the fluorophore using a second spatially modulated pattern comprising alternating high and low intensity regions at a second spatial frequency between 0.1 and 1 mm−1, the second spatially modulated pattern projected onto the surface of the medium at a plurality of different phases, the second spatially modulated pattern having a different spatial frequency than the first spatially modulated pattern, and imaging a pattern of diffusely reflected light emitted by the surface of the medium to form an excitation wavelength image for each phase the plurality of different phases of the second spatially modulated pattern. The images are processed by applying a model of light propagation in an optically absorbing and scattering medium to calculate an absorption coefficient and transport scattering coefficient of the medium at the excitation wavelength of the fluorophore at pixels of the excitation wavelength images. The method also includes determining emissions wavelength optical parameters coefficients at pixels. The method illuminates the surface of the medium with spatially modulated patterns at the excitation wavelength, recording fluorescent emissions wavelength images of the surface of the medium at a third spatial frequency; and while illuminating the surface of the medium with spatially modulated patterns at the excitation wavelength, recording fluorescent emissions wavelength images of the surface of the medium at a fourth spatial frequency. Once the emissions wavelength images are recorded, the method continues with extracting measured modulated amplitude at each of the third and fourth spatial frequencies for pixel regions in the fluorescent emissions wavelength images recorded at the third and fourth spatial frequencies. The method uses the emissions wavelength images to determine depth of the concentration of fluorophore. The third and fourth spatial frequencies comprise at least two spatial frequencies between 0.1 and 0.1 mm−1, and the excitation wavelength and emissions wavelength are both in the "red" portion of the spectrum traditionally known as 630-740 nanometer wavelengths, or in the infrared portion of the spectrum with wavelengths 740 nanometers and longer.

A method designated AC including the method designated A, AA, or AB wherein the spatially modulated patterns comprise a plurality of alternating light and dark bars.

A method designated AD including the method designated A, AA, AB, or AC wherein determining emissions wavelength optical parameters at pixels in the images is performed by a method including irradiating a surface of the medium with a broad beam of light at the emissions wavelength of the fluorophore using a spatially illuminated pattern comprising alternating high and low intensity regions at a fifth spatial frequency between 0.1 and 1 lines per millimeter at each of a plurality of phases; imaging a pattern of diffusely reflected light emitted by the surface of the medium to form an emissions-wavelength, spatially-illuminated, image for the fifth spatial frequency at each of the plurality of phases; irradiating a surface of the medium with a broad beam of light at the emissions wavelength of the fluorophore using a spatially illuminated pattern comprising alternating high and low intensity regions at a sixth spatial frequency between 0.1 and 1 lines per millimeter at each of a plurality of phases; imaging a pattern of diffusely reflected light emitted by the surface of the medium to form an emissions-wavelength, spatially-illuminated, image for the sixth spatial frequency at each of the plurality of phases; and applying a model of light propagation in an optically absorbing and scattering medium to calculate an absorption coefficient and transport scattering coefficient of the medium at the emissions wavelength of the fluorophore at each pixel in the images.

A method designated AE including the method designated A, AA, AB, AC, or AD and further including using the depth of the concentration of fluorophore and at least the absorption coefficient at each pixel to quantify the concentration of fluorophore.

A method designated AF including the method designated A, AA, AB, AC, AD, or AE in which the fluorescent material is protoporphyrin IX.

A method designated AG including the method designated A, AA, AB, AC, AD, AE, or AF further comprising preparing an image with fluorophore concentration encoded as brightness and fluorophore depth encoded as color.

A method designated AH including the method designated AF in which the absorbing and scattering medium is mammalian tissue and the protoporphyrin IX is generated endogenously in the tissue upon administration of 5-aminolevulinic acid.

A method designated AJ including the method designated A, AA, AB, AC, AD, AE, AF, AG, or AH in which the concentration of fluorophore comprises a tumor.

A method designated AK including the method designated A, AA, AB, AC, AD, AE, AF, AG, or AH in which the concentration of fluorophore comprises a molecular material or nanomaterial that fluoresces in the red or near-infrared spectral range from about 600 nm to 1300 nm.

A method designated AL including the method designated AD, AE, AF, AG, AH, AJ, or AK wherein the first, third, and fifth spatial frequencies are the same, the second, fourth, and sixth spatial frequencies are the same, and first and second spatial frequencies differ.

A device designated B for quantifying and determining depth of concentrations of fluorophores includes: an excitation-wavelength light source configurable to excite the fluorophores in the medium using a spatially-modulated light pattern, the spatially-modulated light pattern selectable from a plurality of light patterns with spatial frequencies between 0.1 and 1 lines per millimeter; at least one optical element configured to transfer diffusely-reflected images and fluorescence emission images from the medium to an imaging subsystem; the imaging subsystem comprising at least one filter insertable into the light path to reject light at the excitation wavelength, and at least one electronic camera configured to convert received light into a matrix of digital values according to an intensity of light striking detector pixels; and at least one computer configured to control the spatially-modulated light pattern, to capture images, and configured with machine readable instructions to determine a depth of the concentration of fluorophore and determine a concentration of the fluorophore for image pixels of the camera; and apparatus configured to display fluorophore concentration depth and concentration.

A device designated BA including the device designated B wherein the excitation wavelength is within 100 nanometers of a wavelength peak of fluorescent emissions of the concentration of fluorophore.

A device designated BB including the device designated B or BA wherein the machine readable instructions to determine a depth of a concentration of fluorophore are configured for a method including: extracting measured modulated amplitude at the plurality of spatial frequencies for pixel regions in fluorescent emissions images recorded at a plurality of spatial frequencies; predicting fluorescence modulation for a concentration of fluorophore located at a plurality of depths below the surface of the medium for each spatial frequency of the plurality of spatial frequencies; and fitting the measured modulated amplitude at the plurality of spatial frequencies for pixel regions at the plurality of spatial frequencies to corresponding predicted fluorescence modulation to determine depth of the concentration of fluorophore.

A device designated BC including the device designated B, BA, or BB in which the absorbing and scattering medium is mammalian tissue.

A device designated BD including the device designated B, BA, BB, or BC wherein the excitation wavelength has wavelength between 620 and 640 nanometers.

A device designated BE including the device designated B, BA, BC, or BD wherein the fluorescent emissions wavelength has a peak between 700 and 720 nanometers, as does PpIX.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

We claim:

1. A device for quantifying and determining depth of concentrations of fluorophores in a turbid medium comprising:
   an excitation-wavelength light source configurable to excite the fluorophores in the medium using a plurality of spatially-modulated light patterns having spatial frequencies between 0.2 and 1 lines per millimeter;
   the imaging subsystem comprising at least one filter insertable into a light path from the turbid medium to an electronic camera to reject light at the excitation wavelength; and
   at least one computer configured to control the excitation-wavelength light source, to capture diffusely-reflected images and fluorescence emission images as illuminated using the plurality of spatially-modulated light patterns at a plurality of phases using the electronic camera, and configured with machine readable instructions to determine a depth of the concentration of fluorophore and determine a concentration of the fluorophore for pixels of the diffusely-reflected and fluorescence emission images; and
   apparatus configured to display the fluorophore concentration depth and concentration.

2. The device of claim 1 wherein the machine readable instructions to determine a depth of the concentration of fluorophore are configured for a method comprising:
   extracting measured modulated amplitude at the plurality of spatial frequencies for pixel regions in the fluorescent emissions images recorded at a plurality of spatial frequencies;
   predicting fluorescence modulation for a concentration of fluorophore located at a plurality of depths below the surface of the medium for each spatial frequency of the plurality of spatial frequencies; and
   fitting the measured modulated amplitude at the plurality of spatial frequencies for pixel regions at the plurality of spatial frequencies to corresponding predicted fluorescence modulation to determine depth of the concentration of fluorophore; and
   wherein the excitation wavelength is within 100 nanometers of a wavelength peak of fluorescent emissions of the concentration of fluorophore.

3. The device of claim 2 wherein the machine readable instructions comprise instructions for determining optical properties of the turbid medium at the excitation wavelength, and wherein determining depth of the concentration of fluorophore is performed by a method using the determined optical properties of the turbid medium at the excitation wavelength.

4. The device of claim 3 wherein the machine readable instructions comprise instructions for determining optical properties of the turbid medium at the emissions wavelength, and wherein determining depth of the concentration of fluorophore is performed by a method using the determined optical properties of the turbid medium at the emissions wavelength.

5. The device of claim 4 wherein the determining optical properties of the turbid medium at the emissions wavelength is performed by using an emissions-wavelength light source modulated with a plurality of spatially modulated light patterns spatial modulation frequency between 0.1 and 1 mm−1.

6. The device of claim 5 in which the turbid medium is mammalian tissue.

7. The device of claim 6 wherein the excitation wavelength is between 620 and 640 nanometers.

8. The device of claim 7 wherein the fluorescent emissions wavelength has a peak lying between 700 and 720 nanometers.

9. The device of claim 8, wherein the fluorescent emissions wavelength has a peak lying between 700 and 720 nanometers.

10. The device of claim 5 wherein the camera is a spectrally resolved camera adapted to capture separate images at the fluorescent stimulus and the fluorescent emissions wavelengths.

11. The device of claim 10 wherein the fluorescent stimulus wavelength is red or infrared.

12. The device of claim 11 configured to resolve fluorophore concentrations at depths up to nine millimeters in tissue.

13. The device of claim 12 wherein the spectrally resolved camera is adapted to capture separate images at a first and a second fluorescent emissions wavelength, and the machine readable instructions include instructions for computing ratios of emissions at the first and second fluorescent emissions wavelengths.

14. The device of claim 5 further comprising a phantom having fluorophore concentrations at a plurality of known depths.

15. A device for quantifying and determining depth of concentrations of fluorophores in a turbid medium comprising:
   an excitation-wavelength light source configurable to excite the fluorophores in the medium using a plurality of spatially-modulated light patterns with spatial frequencies between 0.2 and 1 lines per millimeter;
   an optical element configured to transfer light from the turbid medium to an imaging subsystem;
   the imaging subsystem being a spectrally resolved imaging system comprising at least one tunable filter in a light path from the turbid medium to an electronic camera; and
   at least one computer configured to control the spatially-modulated light pattern, to capture diffusely-reflected images and fluorescence emission images using the electronic camera under the plurality of spatially modulated light patterns each at a plurality of phases, and configured with machine readable instructions to determine a depth of the concentration of fluorophore and determine a concentration of the fluorophore for pixels of the diffusely-reflected and fluorescence emission images; and
   apparatus configured to display the fluorophore concentration depth and concentration.

16. The device of claim 15 wherein the machine readable instructions are configured to compute optical parameters of the turbid medium at both excitation and emissions wavelengths.

17. The device of claim 16 wherein:
   the spectrally resolved imaging system is adapted to capture separate images at a first and a second fluorescent emissions wavelength, the machine readable instructions include instructions for computing ratios of emissions at pixels of the images at the first and second fluorescent emissions wavelengths, and the machine readable instructions for determining depth of the concentration of fluorophore use the ratios of emissions at the first and second fluorescent emissions wavelengths in determining depth of the concentration of fluorophore.

18. The device of claim 17 wherein the machine readable instructions to determine a depth of a concentration of fluorophore are configured for a method comprising:

extracting measured modulated amplitude at the plurality of spatial frequencies for pixel regions in fluorescent emissions images recorded at a plurality of spatial frequencies;

predicting fluorescence modulation for a concentration of fluorophore located at a plurality of depths below the surface of the medium for each spatial frequency of the plurality of spatial frequencies from the ratios of emissions at the first and second fluorescent emissions wavelengths; and fitting the measured modulated amplitude at the plurality of spatial frequencies for pixel regions at the plurality of spatial frequencies to corresponding predicted fluorescence modulation to determine depth and concentration of the concentration of fluorophore.

19. The device of claim 18 wherein the machine readable instructions comprise instructions to correct concentration of the concentration of fluorophore using the computed optical parameters of the turbid medium at the fluorescent stimulus and emissions wavelengths.

20. The device of claim 19 wherein the device is capable of resolving concentrations of fluorophore at depths up to nine millimeters in tissue.

21. A method for determining a depth of a concentration of fluorophore lying beneath a surface of an optically absorbing and scattering medium comprising:

illuminating a surface of the medium with a broad beam of light at an excitation wavelength of the fluorophore using a plurality of spatially modulated light patterns each at a plurality of phases and each spatially modulated light pattern comprising alternating high and low intensity regions at spatial frequencies between 0.1 and 1 mm−1;

imaging diffusely reflected light emitted by the surface of the medium to form an excitation wavelength image for each phase of the plurality of different phases of the plurality of spatially modulated pattern;

applying a model of light propagation in an optically absorbing and scattering medium to calculate an absorption coefficient and transport scattering coefficient of the medium at the excitation wavelength of the fluorophore at pixels of the excitation wavelength images;

determining emissions wavelength optical coefficients at pixels;

while illuminating the surface of the medium with a plurality of spatially modulated patterns at the excitation wavelength, recording fluorescent emissions wavelength images of the surface of the medium;

predicting modulated amplitude in images for concentrations of fluorophore located at a plurality of depths below the surface of the medium for each of the plurality of spatially modulated patterns at the excitation wavelength;

fitting modulated amplitude at the plurality of spatially modulated patterns at the excitation wavelength to corresponding predicted modulated amplitudes to determine depth of the concentration of fluorophore.

22. The method of claim 21 where the excitation and emissions wavelength are both red or infrared light of wavelength greater than 630 nanometers.

23. The method of claim 22 wherein the spatially modulated patterns comprise a plurality of alternating light and dark bars.

24. The method of claim 23 wherein determining emissions wavelength optical parameters at pixels in the images is performed by a method comprising:

applying a model of light propagation in an optically absorbing and scattering medium, and using the depth of the concentration of fluorophore and at least the absorption coefficient at each pixel to quantify the concentration of fluorophore.

25. The method of claim 24 in which the fluorescent material is protoporphyrin IX.

26. The method of claim 25 further comprising preparing an image with fluorophore concentration encoded as brightness and fluorophore depth encoded as color.

27. The method of claim 26 in which the absorbing and scattering medium is mammalian tissue, the protoporphyrin IX being generated within the tissue upon administration of 5-aminolevulinic acid.

28. The method of claim 21 in which the concentration of fluorophore comprises a tumor.

* * * * *